United States Patent [19]

Bonwell et al.

[11] Patent Number: 5,335,798

[45] Date of Patent: Aug. 9, 1994

[54] SELF ADHESIVE DENTAL FLOSS DISPENSER

[76] Inventors: Don Bonwell, 5750 Buckingham, Detroit, Mich. 48224; Wayne Veal, 5775 Crane, Detroit, Mich. 48213

[21] Appl. No.: 47,558

[22] Filed: Feb. 19, 1993

[51] Int. Cl.$^5$ .............................................. A47F 5/00
[52] U.S. Cl. ...................................... 211/65; 211/13
[58] Field of Search ................... 211/65, 66, 113, 13, 211/71, 60.1; 340/568

[56] References Cited

U.S. PATENT DOCUMENTS

| | | |
|---|---|---|
| 1,455,673 | 5/1923 | Shalek . |
| 2,413,306 | 12/1946 | Gibson, Jr. ........................ 211/65 |
| 4,140,222 | 2/1979 | Francavilla ........................ 211/65 |
| 5,016,661 | 5/1991 | Israel et al. . |
| 5,097,964 | 3/1992 | Fitz ................................... 211/65 |
| 5,163,566 | 11/1992 | Hempel ............................. 211/65 |

*Primary Examiner*—Robert W. Gibson, Jr.
*Assistant Examiner*—Sarah A. Lechok
*Attorney, Agent, or Firm*—Gossett PLLC Dyekema

[57] ABSTRACT

A dental floss dispenser with floss reminder adapted to hold spools containing threads of the dental floss. Four embodiments of the dispenser are disclosed. Three of the embodiments are mountable on a bathroom wall. Each has a toothbrush rack with projecting pairs of rectangular toothbrush supporting members. In two of the wall mountable embodiments, one of each pair of the toothbrush supporting members houses a semiconductor chip product that has a switch which is activated when a toothbrush is inserted or extracted. The semiconductor chip product emits an auditory sound when activated to remind the user to floss. One embodiment emits a light signal. A caddy holds a conventional floss dispenser. In the third wall mountable embodiment, an electrical circuitry including a signal generator is used instead of the semiconductor chip product. A fourth embodiment is structured as a cup with a cover. A toothbrush inserted through an opening in the cap rests on a disk below which is a semiconductor chip product with a switch. The weight of the disk compresses the switch to activate the semiconductor chip product which emits an auditory signal.

14 Claims, 2 Drawing Sheets

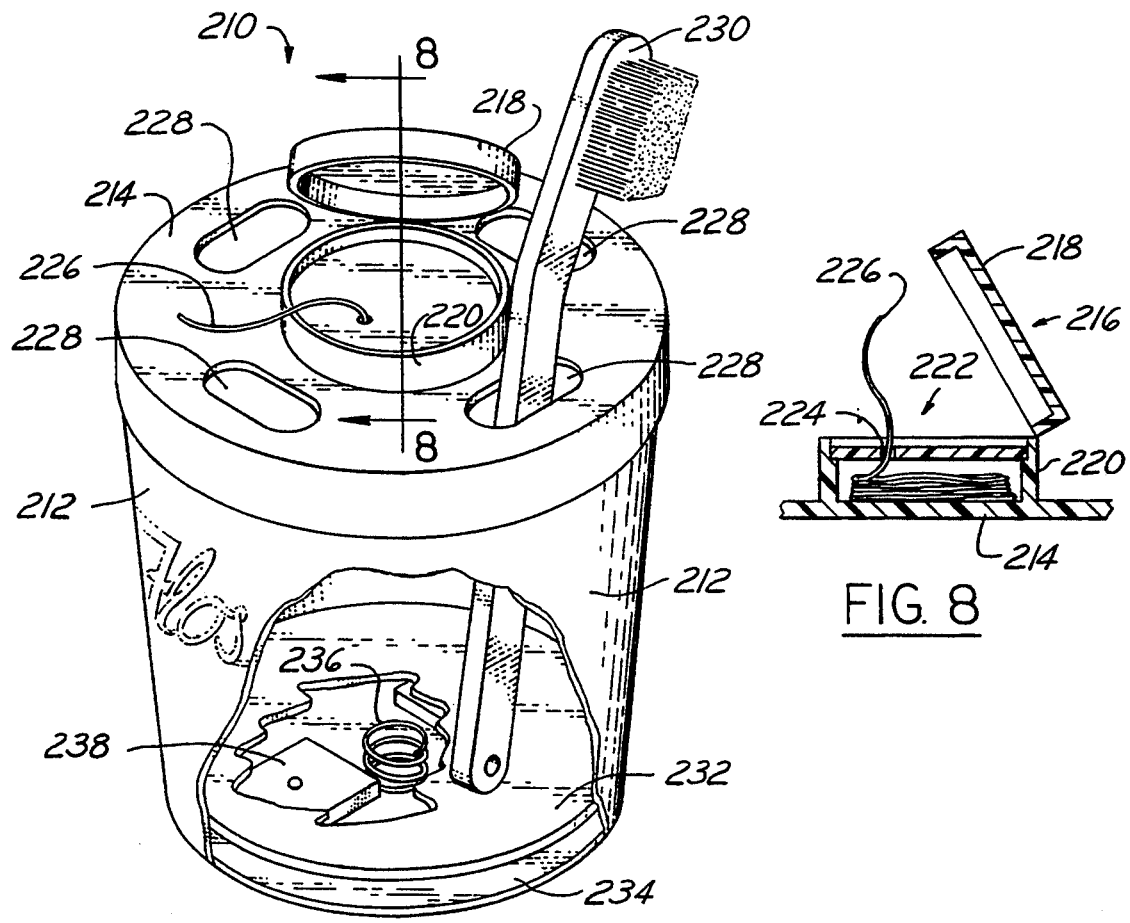
FIG. 7
FIG. 8
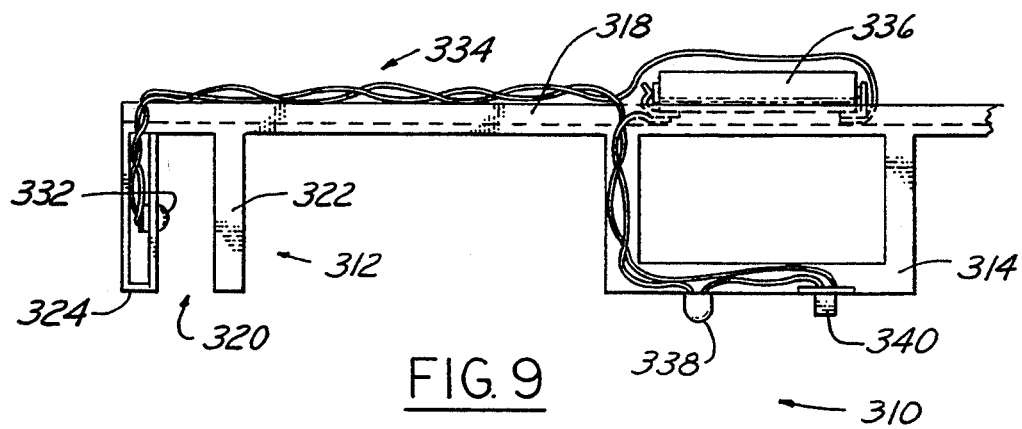
FIG. 9

SELF ADHESIVE DENTAL FLOSS DISPENSER

FIELD OF THE INVENTION

The present invention relates to dental floss dispensers and particularly to dental floss dispensers that remind a person within visual or auditory range of the dispenser to floss his or her teeth. More particularly, the invention relates to a dental floss dispenser and bathroom accessory that reminds a person to floss his or her teeth.

BACKGROUND OF THE INVENTION

1. Need for the Invention

Daily and consistent use of dental floss is known to remove bacterial plaque in proximity to the gums and between the teeth. Dental health care workers, including dentists and oral hygienists, recommend a daily regime of flossing. To induce the habit, it is known to place the floss in a convenient location for easy access and to remind a person in the location to use the dental floss. Generally, by tradition and convenience, such location is a bathroom. But most dental floss containers sold in pharmacies and the like are packaged so as not to encourage a person to place the floss container in the location at a place where the person will be reminded to use the floss. In fact, most floss containers are hidden away in a medicine cabinet or the like.

2. Prior Art

A number of inventions have been proposed to meet the objectives of easy access to dental floss containers and reminding users to use the containers. One example of a dental floss dispenser meeting these objectives can be found in U.S. Pat. No. 1,455,673, issued to Shalek on May 15, 1923. Shalek's device is a dental floss dispenser that has a container which is adapted to hold a spool of dental floss. The container has a cover that may be pivotally opened to present a strand of dental floss which may be guided from the container outside of the container and which may be clipped to break the thread of floss for use by the user. The container has a bracket for securing it to a wall, preferably a bathroom wall adjacent a wash bowl.

Another example can be found in U.S. Pat. No. 5,016,661 issued to Israel et al. on May 21, 1991. Israel et al. discloses a dental floss container holder and floss dispenser that has a housing with a front and back portion. A contoured resilient material that is made of closed or opened cell foam or neoprene is affixed to the interior of the housing. The resilient material will retain variously shaped dental floss containers and spools. A cutter is position on the exterior of the housing, which is wall mountable.

While the two foregoing examples meet the objective of having the dental floss container convenient to remind a person to use the dental floss, they are not always successful. This is particularly true in that flossing usually is done in early morning when a person may not be fully awake so as to be sensitive to such hygienic demands or in the evening when a person is so tired as to forget the least pressing preparation before retiring to bed. Israel et al. manages to disclose a possible device that would provide a better reminder to the person. As an aside, Israel et al. suggests that "a timing device or alarm device to serve as a reminder to floss daily," may be used with their invention. But Israel et al. failed to tell just how such a device would be used and so do not provide a disclosure that one of ordinary skill in the art would be prepared to incorporate into such a dispenser without his or her own invention of the device.

OBJECTS OF THE INVENTION

Accordingly, it is one object of the present invention to provide a dental floss dispenser with a reminding device to remind a person to floss daily and to disclose the device in such a way that one of ordinary skill in the art can make and use such a device.

It is another object of the present invention to provide a dental floss dispenser that has means to remind a person, who is within a visual or auditory range of the dental floss dispenser, to floss.

It is yet another object of the present invention to provide a dental floss dispenser with an auditory or visual device that will remind the person to floss daily or an auditory and visual device to remind the same, but which is housed in a manner that it might be incorporated into a bathroom decor with easy access and use.

SUMMARY OF THE INVENTION

A wall mountable dispenser for holding dental floss is adapted to hold spools containing threads of the dental floss. The dental floss dispenser with floss reminder may be mounted on a vertical surface, such as a bathroom wall, by a screw or an adhesive or other means known to those of ordinary skill in the art.

The dental floss dispenser with floss reminder has a toothbrush rack and a dental floss caddy. The dental floss caddy is a pocket capable of holding a variety of conventionally sized, if not standard sized, commercial dental floss dispensers. Preferably, the dental floss caddy is disposed between two toothbrush racks. The toothbrush rack comprises a beam from which pairs of rectangular toothbrush supporting members project. One of each pair of toothbrush supporting members is a simple support member. The other is a switch support member that has a cavity in which a semiconductor chip product is housed. The semiconductor chip product may be extracted from the cavity and can be programmed to provide a reminder message such as a simple electronic beeping sound or a musical cue or a voice message such as "Don't forget to floss!". The semiconductor chip product is activated by a switch and has circuitry known to those of ordinary skill in the art.

When a toothbrush is removed from a a pair of toothbrush supporting members, the switch on the semiconductor chip product is activated, causing the semiconductor chip product to emit its auditory signal The user is reminded to floss and reaches for the dental floss dispenser and flosses his or her teeth. If the user forgets to floss before returning the toothbrush to the toothbrush supporting members, the semiconductor chip product is activated when it is returned, again reminding the user to floss.

Another embodiment of the present invention is but a slight modification with a switch support member, adapted with a notch to accommodate an indicator light that is incorporated into the outer structure or housing of a semiconductor chip product. Thus, instead of an auditory signal, the semiconductor chip product emits a light signal upon activation.

Yet another embodiment of the invention is structured as a covered cup having a bottom cup portion and a top cover portion. The top cover has a dental floss dispenser formed onto it and a plurality of openings through which toothbrushes may be inserted for support within the bottom cup portion of this embodiment of the dental floss dispenser with floss reminder. The toothbrush rests upon a circular disc that has a diameter slightly less than the diameter of the base of the bottom cup portion. Attached to the bottom of the disc, as the disc is placed within the bottom cup portion, is a spring. The spring is preferably attached to the center of the base and is of low compressive spring force so that it does not support the eccentric weight of a toothbrush pressing downwardly on the disc, but of sufficient strength to support the disc above semiconductor chip product placed on the base.

Still yet another embodiment of the invention is a wall mountable dispenser for holding dental floss and toothbrushes and for housing indicator means to remind a user that he or she should floss his or her teeth. A toothbrush rack comprises a beam from which at least one pair of rectangular toothbrush supporting members project, one of the pair being a simple support member and the other being a switch support member. The switch support member has a switch and has circuitry known to those of ordinary skill in the art. The circuitry is connected to an indicator light and another switch mounted on a dental floss caddy. When a toothbrush is removed from the pair of toothbrush supporting members, the switch in the switch support member is activated, causing the indicator light on the dental floss caddy to emit its visual signal that reminds a user to floss. The indicator light continues to emit its visual signal until the switch on the dental floss caddy is depressed to turn off the signal.

BRIEF DESCRIPTION OF THE DRAWINGS

FIG. 7 is a perspective view of another yet embodiment of the dental floss dispenser with floss reminder.

FIG. 8 is a partial sectional view, taken in the direction of arrows 8—8 in FIG. 7, of the dental floss dispenser.

FIG. 9, a plan view of yet another embodiment of a dental floss dispenser with floss reminder.

DETAILED DESCRIPTION OFT HE PREFERRED EMBODIMENT

Figure 1:
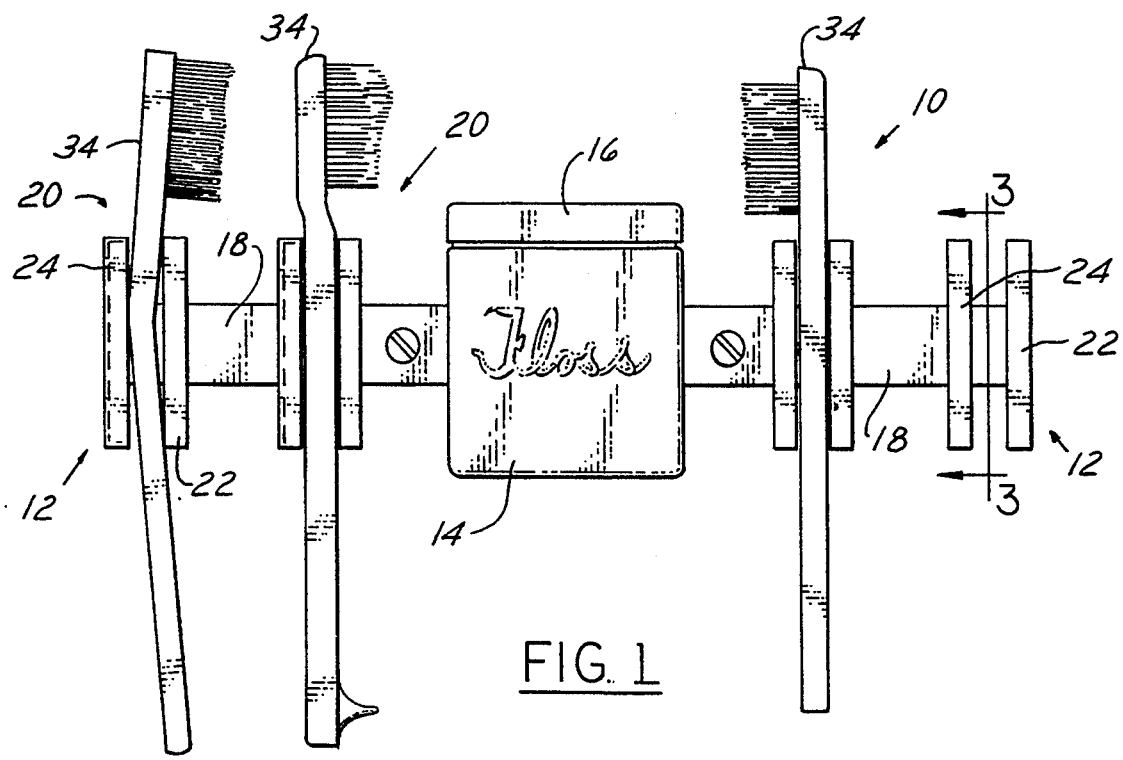
FIG. 1 is a front elevation of a first embodiment of a dental floss dispenser with floss reminder in accordance with the invention.

Four embodiments of the invention are shown in the drawings as examples of its principles and not as a limitation on the scope of the invention or the claims.

Figure 2:
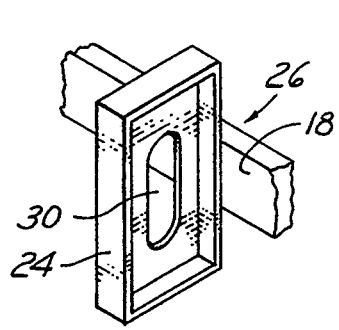
FIG. 2 is a partial perspective view of the dental floss dispenser with floss reminder showing a switch support member as a part of the invention.
Figure 4:
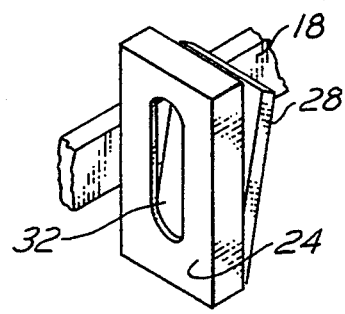
FIG. 4 is a partial perspective view of the dental floss dispenser with floss reminder showing a switch support member shown in FIG. 2 from a different perspective and with a switch partially therein.

Referring to FIG. 1, an elevation of one of the preferred embodiments is shown as a dental floss dispenser with floss reminder 10 for holding dental floss and toothbrushes and for housing indicator means to remind a user that he or she should floss his or her teeth. The dental floss dispenser with floss reminder 10 may be mounted on a vertical surface, such as a bathroom wall. As seen in both FIGS. 1 and 2, the dental floss dispenser with floss reminder 10 is mounted with a screw, but it may also be mounted by an adhesive or other means known to those of ordinary skill in the art of securing bathroom shelving and other such fixtures to the walls of bathrooms.

The dental floss dispenser with floss reminder 10 has a toothbrush rack 12 and a dental floss caddy 14. The dental floss caddy 14 is a pocket capable of holding a variety of conventionally sized, if not a standard sized, commercial dental floss dispensers 16, that is dental floss dispensers with dental floss therein, as sold in drug and grocery stores, etc. Preferably, the dental floss caddy 14 is disposed between two toothbrush racks 12 to draw attention to the dental floss caddy 14. The toothbrush rack 12 comprises a beam 18 from which pairs of rectangular toothbrush supporting members 20 project. One of each pair of toothbrush supporting members 20 is a simple support member 22.

Figure 3:
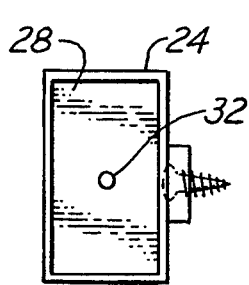
FIG. 3 is an elevational view, taken in the direction of arrows 3—3 in FIG. 1, of the switch support member of FIG. 2 with a switch inserted therein.
Figure 5:
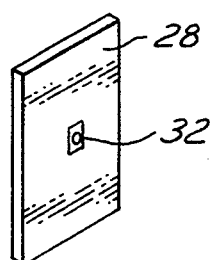
FIG. 5 is a perspective view of the switch shown in FIG. 3.

Referring to FIGS. 2–5, along with FIG. 1, the other of each pair of toothbrush supporting members 20 is a switch support member 24. The switch support member has a cavity 26 (FIG. 2) into which a semiconductor chip product 28 is housed (FIG. 3). The semiconductor chip product may be extracted from the cavity 26 by pressing against the semiconductor chip product 28 with a tool, through an opening 30. The semiconductor chip product 28 can be programmed to provide a reminder message such as a simple electronic beeping sound or a musical cue or a voice message such as "Don't forget to floss!". The semiconductor chip product 28 is activated by a switch 32 and has circuitry known to those of ordinary skill in the art, such as in products sold as novelty items placed in toilet paper rolls for activation to produce sounds when the toilet paper is pulled forcing the roll cardboard core against the supporting spool.

With reference again to FIG. 1, according to this first embodiment, when a toothbrush 34 is removed from a pair of toothbrush supporting members 20, the switch 32 on the semiconductor chip product 28 is activated, causing the semiconductor chip product 28 to emit its auditory signal, such as "Don't forget to floss!". The user of the dental floss dispenser with floss reminder 10 is reminded to floss and reaches for the dental floss dispenser 16. If the user forgets to floss before returning the toothbrush 34 to the toothbrush supporting members 20, the semiconductor chip product 28 is activated when it is returned, again reminding the user to floss.

Figure 6:
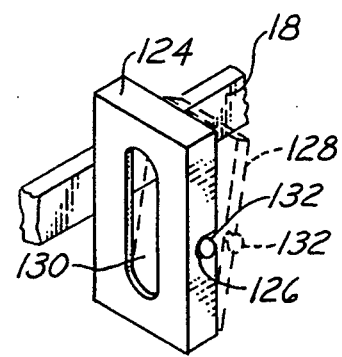
FIG. 6 is a partial perspective view of another embodiment of the dental floss dispenser with floss reminder showing a switch support member with a switch partially therein.

As may be seen with reference to FIG. 6, another embodiment of the present invention is but a slight modification of the embodiment described above. The structure of the dental floss dispenser with floss reminder 10 is the same but for the switch support member 124, which is adapted with a notch 126 to accommodate an indicator light 132. Indicator light 132 is incorporated into the outer structure or housing of a semiconductor chip product 128. Thus, instead of an auditory signal, the semiconductor chip product 128 emits a light signal upon activation of the semiconductor chip product switch as explained with reference to the first embodiment described above.

Yet another embodiment of the invention may be explained with reference to FIG. 7. A dental floss dispenser with floss reminder 210 is structured as a covered cup having a bottom cup portion 212 and a top cover portion 214. The top cover 214 has a dental floss dispenser 216 formed onto it. The dental floss dispenser 216 has a cap 218 and a well wall 220, creating a well 222 in which dental floss 224 may be housed. Preferably, the well 222 is cylindrical, and the cap 218 circular, but the well 222 may be surrounded by a number of walls, for example, four to create a rectangular well 222. A rectangular cap is preferable for a rectangular well 222. Preferably, the cap 218 is attached to the well wall 220 by a living hinge. The floor of the well 222 is the cover portion 214. The dispenser 216 has a floss cutter blade 224 attached to the well wall 220, for cutting a floss strand 226 to a desired length.

The top cover portion 214 has a plurality of openings 228 through which a toothbrush 230 may be inserted for support within the bottom cup portion 212 of the dental floss dispenser with floss reminder 210. The toothbrush 230 rests upon a circular disc 232 that has a diameter slightly less than the diameter of the base 234 of the bottom cup portion 212. Attached to the bottom of the disc 232, as the disc 232 is placed within the bottom cup portion 212 so that its bottom is adjacent the base 234 of the bottom cup portion 212, is a spring 236. Spring 236 is preferably attached to the center of the base 234 of the dental floss dispenser with floss reminder 10 and is of low compressive spring force so that it does not support the eccentric weight of a toothbrush 230 pressing downwardly on the disc 232, but of sufficient strength to support the disc 232 above semiconductor chip product 238 placed on the base 232 of the bottom cup portion 212.

Referring to the FIG. 9, a plan view of yet another embodiment of a dental floss dispenser with floss reminder 310 for holding dental floss and toothbrushes and for housing indicator means to remind a user that he or she should floss his or her teeth. The dental floss dispenser with floss reminder 310 is mounted on a vertical surface, as the first discussed embodiment in FIG. 1. The dental floss dispenser with floss reminder 310 has a toothbrush rack 312 and a dental floss caddy 314. The dental floss caddy 314 is a pocket capable of holding a dental floss dispenser, again as the embodiment in FIG. 1. The toothbrush rack 312 comprises a beam 318 from which at least one pair of rectangular toothbrush supporting members 320 project. One of each pair of toothbrush supporting members 320 is a simple support member 322, while the other of each pair of toothbrush supporting members 320 is a switch support member 324. The switch support member has a switch 332 and has circuitry 334 energized by a small battery 336, as is known to those of ordinary skill in the art. An indicator light 338 and another switch 340 are connected to the circuitry 334.

When a toothbrush is removed from the pair of toothbrush supporting members 320, the switch 332 is activated, causing the indicator light 336 to emit its visual signal that reminds a user to floss. The indicator light continues to emit its visual signal until the switch 338 is compressed to turn off the signal.

While what has been shown is considered to be the preferred embodiments of the invention, it is desired to secure the appended claims all modification as fall within the true spirit and scope of the invention.

We claim:

1. A dental floss dispenser with floss reminder to remind a user to floss when the user moves a toothbrush from one to another of two dispositions, the two dispositions including a first disposition being where the toothbrush is supported by a toothbrush supporting means of the dental floss dispenser and a second disposition being where the toothbrush has been taken from said supporting means, the dental floss dispenser comprising:

said toothbrush supporting means for supporting the toothbrush therein;

switch means for exciting a signal means when said switch means is brought into operation when said toothbrush is moved from one disposition to the other;

a dental floss caddy attached to said toothbrush supporting means, said toothbrush caddy for holding dental floss therein; and said signal means operatively connected to said switch means so that said signal means is excited when said switch means is brought into operation.

2. The dental floss dispenser with floss reminder of claim 1, wherein said switch means excites said signal means when said switch means is initially depressed and when said switch means is initially released, said switch means being initially depressed when a toothbrush is moved from said second disposition to said first disposition and said switch means being initially released when said toothbrush is moved from said first disposition to said second disposition.

3. The dental floss dispenser with floss reminder of claim 2, wherein said toothbrush supporting means includes a beam and at least one toothbrush rack attached to said beam, said toothbrush rack including a pair of toothbrush supporting members projecting from said beam for supporting a toothbrush between said toothbrush supporting members, at least one of said pair of toothbrush supporting members having said switch means attached thereto, said switch means being initially depressed when a toothbrush is inserted between said supporting members and being initially released when said toothbrush is taken from between said supporting members, and wherein said dental floss caddy is attached to said beam, said dental floss caddy having a pocket for holding a commercial dental floss dispenser.

4. The dental floss dispenser with floss reminder of claim 3, wherein said at least one of said pair of toothbrush supporting members having switch means has a cavity for housing a semiconductor chip product therein and said switch means and said signal means are contained in a semiconductor chip housed in said cavity.

5. The dental floss dispenser with floss reminder of claim 3, further comprising circuitry, including battery means, and wherein said signal means is operatively connected to said switch means by said circuitry.

6. The dental floss dispenser with floss reminder of claim 3, wherein said toothbrush supporting means is a covered cup having a bottom cup portion including a base and a top cover portion, the dental floss dispenser being attached to the top cover portion, the top cover portion having at least one opening through which a toothbrush may be inserted for support within the bottom cup portion, and the supporting means including a circular disc having a diameter slightly less than the diameter of the base of the bottom cup portion, the supporting means also including a spring attached to the bottom of the disc as the disc is placed within the bottom cup portion so that the bottom of the disc is adjacent the base of the bottom cup portion, the spring having a low compressive spring force so that the spring does not support the eccentric weight of a toothbrush pressing downwardly on the disc, and wherein said switch means and said signal means are contained in a semiconductor chip place on the base of the bottom cup portion, below the disc.

7. A dental floss dispenser with floss reminder, comprising:
a beam;
at least one toothbrush rack attached to said beam, said toothbrush rack including a pair of toothbrush supporting members projecting from said beam for supporting a toothbrush between said toothbrush supporting members, at least one of said pair of toothbrush supporting members having switch means for exciting a signal means when said switch means is initially depressed and when initially released, said switch means being initially depressed when a toothbrush is inserted between said supporting members and being initially released when said toothbrush is taken from between said supporting members;
a dental floss caddy attached to said beam, said toothbrush caddy having a pocket for holding a dental floss dispenser; and
said signal means operatively connected to said switch means.

8. The dental floss dispenser with floss reminder of claim 7, wherein said at least one of said pair of toothbrush supporting members having switch means has a cavity for housing a semiconductor chip product therein and said switch means and said signal means are contained in a semiconductor chip housed in said cavity.

9. The dental floss dispenser with floss reminder of claim 7, further comprising circuitry, including battery means, and wherein said signal means is operatively connected to said switch means by said circuitry.

10. A dental floss dispenser with floss reminder, comprising:
a beam;
at least one toothbrush rack attached to said beam, said toothbrush rack including a pair of toothbrush supporting members projecting from said beam for supporting a toothbrush between said toothbrush supporting members, at least one of said pair of toothbrush supporting members having a cavity for housing a semiconductor chip product therein;
a dental floss caddy attached to said beam, said toothbrush caddy having a pocket for holding a dental floss dispenser; and
a semiconductor chip product housed in said cavity, said semiconductor chip product having a switch and said switch being capable of emitting an auditory signal when said switch is compressed.

11. The dental floss dispenser with floss reminder of claim 10, wherein said switch is compressed when a toothbrush is inserted between said toothbrush supporting members.

12. The dental floss dispenser with floss reminder of claim 10, wherein the semiconductor chip product may be extracted from the cavity.

13. The dental floss dispenser with floss reminder of claim 12, wherein said cavity has opposing openings so that by pressing through one of said opposing openings, against one side of the semiconductor chip product, will cause said semiconductor chip product to be extracted through said opposing opening.

14. The dental floss dispenser with floss reminder of claim 11, wherein, when a toothbrush is removed from said pair of toothbrush supporting members, said switch is activated to causing said semiconductor chip product to emit said auditory signal.

* * * * *